United States Patent [19]
Edelson et al.

[11] 3,969,440
[45] July 13, 1976

[54] PHOSPHORUS CONTAINING ACRYLIC ESTERS AND AMIDES

[75] Inventors: Nathan Allen Edelson, Cynwyd; Robert W. Faessinger, Media, both of Pa.

[73] Assignee: Scott Paper Company, Philadelphia, Pa.

[22] Filed: Apr. 7, 1975

[21] Appl. No.: 565,413

Related U.S. Application Data

[60] Division of Ser. No. 508,724, Sept. 23, 1974, Pat. No. 3,926,872, which is a continuation-in-part of Ser. No. 325,101, Jan. 19, 1973, abandoned.

[52] U.S. Cl. .............................. 260/944; 260/486 R; 260/561 N; 260/561 P; 260/952
[51] Int. Cl.² ........................ C07F 9/02; C07F 9/22
[58] Field of Search ............... 260/944, 952, 486 R, 260/561 N, 561 P

[56] References Cited
UNITED STATES PATENTS

| | | | |
|---|---|---|---|
| 2,401,440 | 2/1942 | Thomas | 8/116 |
| 2,955,015 | 10/1960 | Segro | 8/116 |
| 3,346,545 | 10/1967 | Sehm | 260/89.7 |
| 3,351,617 | 11/1967 | Jaeger | 260/89.7 |
| 3,359,224 | 12/1967 | Faessinger et al. | 260/17.4 |
| 3,519,607 | 7/1970 | Welch | 260/80 |
| 3,524,901 | 8/1970 | Najvar | 260/80 |
| 3,583,938 | 6/1971 | Okada et al. | 8/194 |
| 3,766,252 | 10/1973 | Schmidt et al. | 260/486 |

FOREIGN PATENTS OR APPLICATIONS

| | | | |
|---|---|---|---|
| 736,508 | 6/1966 | Canada | 260/139.5 |
| 1,202,869 | 1/1960 | France | 260/944 |
| 1,594,915 | 8/1969 | Germany | |
| 829,576 | 2/1960 | United Kingdom | 260/561 |
| 877,905 | 9/1961 | United Kingdom | 260/952 |
| 894,719 | 4/1962 | United Kingdom | 260/952 |

Primary Examiner—Howard E. Schain
Assistant Examiner—Edward Woodberry
Attorney, Agent, or Firm—N. J. DeBenedictis; J. W. Kane

[57] ABSTRACT

Flame-retardant acrylic-phosphato esters or amides suitable for grafting to cellulosic fibers to produce essentially permanently fire-retardant cellulosic fibers.

6 Claims, No Drawings

PHOSPHORUS CONTAINING ACRYLIC ESTERS AND AMIDES

RELATED APPLICATION

This is a division of application Ser. No. 508,724 filed Sept. 23, 1974, and now U.S. Pat. No. 3,926,872, which is a continuation in part of application Ser. No. 325,101, filed Jan. 19, 1973 now abandoned.

BACKGROUND OF THE INVENTION

1. Field of the Invention

This invention relates to specific acrylic esters and amides that can be graft copolymerized onto a cellulosic substrate to impart essentially permanent fire retardant properties to a cellulosic substrate and to cellulosic substrates copolymerized with said compounds.

2. Description of the Prior Art

Cellulosic textiles are very flammable especially when in a napped or brushed form. This hazard has been recognized for many years and a variety of methods have been employed to suppress this flammability. Some methods achieved a high level of nonflammability but were not permanent, that is, their flame retardancy was lost after one or more washings. Other methods imparted essentially permanent flame retardancy although they seriously impaired the textile qualities of the cellulosic material.

Cotton, linen and other cellulosic fibrous materials in fabric form have been impregnated with phosphoric acid, organic or inorganic ammonium salts of phosphoric acid, sulfonic acid or its organic and inorganic ammonium salts, borax, boric acid, ammonium borate and the like in order to render the cellulosic fabric flame retardant and in some cases self-extinguishing. However, such reagents usually do not combine chemically or physically to the fabric and water leaches out the beneficial fire retardant property.

Thermosetting resins, rich in phosphorus and nitrogen, have been devised which when patted on the cellulosic substrate and consequently cured with heat in the presence of a catalyst, improves the permanent (durable) nature of the non-flammable characteristic of the treated fabric. Flame retardancy achieved by this technique usually is durable to a number of home launderings but the fabric so treated suffers from a loss of hand, loss of tear strength and a reduction in abrasion resistance through a stiffening of the textile structure.

Reduced flammability may be imparted to synthetic cellulosic fiber such as rayon, during its manufacture by incorporating a fire retarding reagent in the viscose dope. Subsequent regeneration of such a treated dope yields cellulose (rayon) having the fire retarding reagent physically entrapped within its structure. Such fire retarding reagents must be inert to the high alkalinity of viscose dope, be capable of passing freely through the extremely fine orifice of the rayon spinnerette and capable also of withstanding the action of the highly acidic regeneration bath and subsequent finishing steps of the rayon process. In addition, the reagent should be insoluble in water and the usual dry cleaning solvents. To satisfy all these requirements is both costly and technically difficult.

Graft copolymerization of cellulosics (fiber or fabric) with a phosphorous or halogen containing vinyl compound has been shown to impart a degree of flame retardancy to the grafted substrate. The presence of amino (or amido) nitrogen groups enhances the fire retardant action. However, halogen containing vinyl compounds should have a relatively labile halogen atom in order to be effective but with such compounds the grafted cellulosic substrate gradually loses strength through the depolymerization of its cellulose backbone by the catalytic action of the halogenic acid being slowly liberated.

SUMMARY OF THE INVENTION

Acrylic esters or amides of the following general formula:

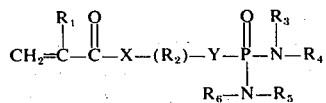

wherein $R_1$ = hydrogen or methyl; $R_2$ is a lower substituted or unsubstituted alkylene group, $R_3$, $R_4$, $R_5$ and $R_6$ are selected from the group consisting of methyl and ethyl; X = O or —NH—; and Y = O or —NH—. The flame retardant monomers defined by the general formula when graft copolymerized onto a cellulosic substrate impart flame retardancy to the resulting novel graft copolymerized product. With reference to the general formula, $R_2$ is a lower alkylene group connecting the X and Y atoms and preferably has 1 to 3 carbon atoms. This alkylene group can be substituted or unsubstituted with substituents such as halogen or other substituents that do not prevent the flame retardant ability of the monomer when grafted onto cellulosic substrates. Those skilled in the art could readily develop benign substituents for the alkalene group and still obtain compounds employing the discovery disclosed herein.

DETAILED DESCRIPTION OF THE PREFERRED EMBODIMENTS

The grafting of a monomer of the above general formula onto a cellulosic fiber or fabric results in a permanently fire retardant cellulosic product that is capable of withstanding at least about 50 home launderings or dry cleanings. The particular method employed for grafting the monomer onto the cellulosic substrate is not critical and there are many known techniques for grafting such monomers onto cellulosic substrates. Examples of such techniques are disclosed in U.S. Pat. No. 2,955,015 issued to M. Segrow, et al; U.S. Pat. No. 3,083,118 issued to D. J. Bridgefort; and U.S. Pat. No. 3,359,224 issued to Paessinger et al, which patents are incorporated herein by reference as if fully reprinted herein. The preferred method is the grafting techniques described in U.S. Pat. No. 3,359,224 with the monomers of Examples II or IX.

The novel monomers of this invention may be graft copolymerized onto the cellulosic fiber before or after it is made into a fabric. When copolymerized onto a cellulosic fabric, the fabric can be all cellulosic fibers or a blend of cellulosic fibers with noncellulosic fibers or yarn. However, the non-cellulosic fiber content of the blended fabric will not be rendered fire retardant by the monomers of the present invention. Therefore, the flame retardancy of a fabric blend also depends upon the amount and flammability of the non-cellulosic component.

The amount of monomers graft copolymerized onto the cellulosic substrate depends upon the degree of flame retardancy desired. Preferably, sufficient monomers should be graft copolymerized onto the substrates so that the resulting product contains at least about 0.5% phosphorus based upon the total weight of the graft copolymerized product. Between 1.5 and 3.5% phosphorus content is particularly preferred. Phosphorus contents above 3.5 to about 5.6% are very effective while phosphorus contents above about 5.0% while effective are less economical than the preferred phosphorus contents since the increased cost for large amounts of monomers may not justify the difference in flame retardancy imparted by the greater monomer added on to the substrate. However, there is no exact upper limit to the amount of monomer that can be grafted onto the cellulosic substrate, the main consideration being an economic one. Furthermore, the monomers of the present invention may be used in combination with other monomers in order to achieve a higher nitrogen content on the resulting graft copolymerized product or to impart properties in addition to fire retardancy. Cellulosic containing fabrics that have been graft copolymerized with monomers of the present invention may thereafter be further treated with permanent press resins (wrinkle resistant) with little or no less in the substrate's strength, characteristics or loss in hand.

EXAMPLE I

A 4-neck 1 liter flask equipped with an Inframo Electrical stirrer, a water-condenser, a pressure equalizing spearatory funnel and a thermometer was charged with 500 mls. dry diethyl ether; 76.5 g. (0.5 mole) phosphorus oxychloride; 50.5 g. (0.5 mole) dry triethylamine; and 68 g (0.5 mole) dry 2-hydroxyethylmethacrylate. During the addition of reagents, the temperature of the flask's contents was controlled in the −10°C to 10°C. temperature range. After stirring the reaction mixture at room temperature for a suitable reaction time (72 hrs.), triethylamine hydrochloride was filtered off at an essentially quantitative yield. The filtrate was placed back into the reaction flask without isolation of the dichlorophosphatoethyl methacrylate intermediate. The reaction flask was then charged with 101 g. (1 mole) dry triethylamine and 45 g. (1 mole) dry dimethylamine. The addition of the two amines was accomplished in the −10° to 10°C range and afterwards the reaction mixture was stirred at room temperature for a suitable reaction period (72 hrs.). The reaction mixture was next filtered to remove the triethylamine hydrochloride by-product and the volatile impurities; then diethyl ether was removed by distillation. Methacryloxyethylorthophosphorotetramethyldiamidate was obtained at a yield of 60% of the theoretical for the two step reaction sequence. This is a compound of the general formula in which $R_1$, $R_3$, $R_4$, $R_5$ and $R_6$ all equal —$CH_3$; X and Y = O; and $R_2$ is —$C_2H_4$—. The properties are the same as reported in Example II.

EXAMPLE II

This example involved identical reagents, reaction times, temperatures and purification steps to Example I. The difference between the two procedures involved the use of reactants in a different order of addition. Example II eliminates the troublesome addition side reaction of dimethylamine to 2-hydroxyethylmethacrylate which can occur. The reaction flask was first charged with dry diethyl ether (500 mls.). 76.5 g. (0.5 mole) phosphorus oxychloride; 101 g. (1 mole) dry triethylamine; and 45 g. (1 mole) dry dimethylamine. After stirring the reaction mixture at room temperature for 3 days, the triethylamine hydrochloride was filtered off. A small portion of the filtrate was concentrated and then distilled (b.p. 23°–95°C. at 4mm. pressure) to give pure bis(dimethylamido) chlorophosphate containing 17.8% phosphorus by analysis compared to the calculated value of 18.2%. Vapor phase chromatograph analysis of the filtrate showed this intermediate to be obtained in an 80% yield of the theoretical.

The major portion of the filtrate, without benefit of purification by distillation was charged again into the reaction flask and reacted in a second step with 63 g. (0.5 mole) dry 2-hydroxyethylmethacrylate and 50.5 g. (0.5 mole) dry triethylamine. After reaction at room temperature for 72 hours, the solvent and volatile impurities were removed by flash evaporation. The residue was then distilled to give essentially pure Methacryloxyethylorthophosphorotetramethyldiamidate which is colorless, water soluble, liquid possessing an amine-like odor and a boiling point of 140.5°–141°C. at 4 mm. pressure. The vapor phase chromatography analysis of the material showed greater than 99% purity. In addition, the infrared spectrum was shown to be consistent with the proposed structure. Other physical properties include index of refraction at 20°C. = 1.4605; density at 25°C. = 1.108; % N calc. 10.6, % N observed 10.5; % P calc. 11.7, % P observed 12.0. The material was synthesized in a 65% overall yield of the theoretical.

EXAMPLE III

Run 3a. In accordance with the teachings of U.S. Pat. No. 3,359,224, an approximately 10 gram piece of circular rayon Knit was dithiocarbonated for 15 minutes in 250 mls. of an emulsion prepared from 1% sodium hydroxide, 0.96% carbon disulfide and 2 drops of an alkylaryl polyether alcohol surfactant (Rohm and Haas' Triton X-155). The dithiocarbonated substrate was next thoroughly washed with distilled water and suspended for a few minutes in a 200 ml. solution containing 0.004% Mohr's salt (ferrous ammonium sulfate). Following this, the ferrated substrate was washed with distilled water and suspended in a monomer system consisting of hydrogen peroxide (3 ml. of 30% solution), the monomer from Example II, Methacryloxyethylorthophosphorotetramethyldiamidate (5 grams), and 500 ml. $H_2O$. The polymerization was maintained in a rotating oven for 2½ hours at 55°–57°C. following which, the rayon substrate was washed thoroughly with tap water and suspended for a few minutes in a 0.2% sodium bisulfite solution. The graft product was thoroughly washed with water and oven dried at 100°–110°C. for 2 hours. A conversion of monomer to polymer of 56% was achieved.

The procedure of Run 3a was repeated two additional times thereby resulting in runs 3(a), 3(b) and 3(c). This repetition of Run 3a was done in order to determine the consistency of the graph copolymerization process and the product obtained thereby. The graft copolymerized product of runs 3(a), 3(b) and 3(c) were subjected to 50 washes and then tested for Vertical Flame rating according to ASTM standard Test D 626-551. The samples were also tested for % phosphorus and % nitrogen present after graft copolymerization had taken place and also after the sample was subjected to 59 washes. The results are reported in Table I appearing at the end of this specification.

EXAMPLE IV

The procedure of Example III was repeated with the monomer of Example II with the exception that the monomer was purified by distillation before it was used in the process of Example III. The results are reported in Table I as run Ex. 4. The major difference in the results of Example IV vs. the results of Example III is in the grafting efficiency, that is, the percent of the monomer that was grafted onto the cellulosic substrate. When the monomer was purified by distillation prior to the graft copolymerization, essentially 100% of the monomer was grafted onto the substrate while in Examples III(a) (b) (c) approximately 50% of the monomer was grafted on to the substrate.

EXAMPLE V

Methacryloxyethylorthophosphorotetramethyldiamidate monomer from Example II (7 grams) was added to a solution of 250 ml. water containing a small quantity of a quaternary ammonium surfactant. A 10 gram piece of rayon circular knit sock was added to the system, the system sparged with nitrogen, and 10 ml. of $Ca(NH_4)_2$.$(NO_3)_6$ 0.1 M in $HNO_3$ was added and graft copolymerization was carried out in accordance with the teachings of U.S. Pat. No. 2,955,015. The reaction mixture was maintained at room temperature with a nitrogen sparge for 2 hours. A percent conversion of monomer to grafted polymer of 50% was obtained and the resulting graft product was flame retardant as measured by the Vertical Flame Test ASTM Standard D 626-551 (3″ char, rating of 2).

EXAMPLE VI

A ferrous/hydrogen peroxide redox graft copolymerization was also carried out in the manner described in U.S. Pat. No. 3,083,110. A rayon circular knit sock (10 g.) was soaked first in a 0.2% Mohr's salt solution for ten minutes at room temperature and then was heated at 60°–70°C. for 4 hours in the polymerization medium consisting of 500 ml. water, 3 ml. 30% hydrogen peroxide, a polyoxyethylene sorbitan trioleate surfactant and 7 grams of methacryloxyethylorthophosphorotetramethyldiamidate prepared according to Example II. The percent conversion of monomer to grafted polymer was 78% of the theoretical. The resulting graft product was shown to be flame retardant as measured by the Vertical Flame Test 1¾″ char, rating of 2).

EXAMPLE VII

A 4-neck 1 liter flask equipped with an Inframo Electrical stirrer, a water condenser, a pressure equalizing separatory funnel and a thermometer was charged with 500 ml. dry diethyl ether; 76.5 g. (0.5 mole), phosphorus oxychloride; 50.5 (0.5 mole) dry triethylamine; and 62 g. (0.5 mole) of dry 2-hydroxyethylmethacrylate. The addition of reagents was controlled in the −10° to 10°C. temperature range. The reaction mixture was stirred at room temperature for a suitable reaction time (72 hrs.) and triethylamine hydrochloride was filtered off in essentially a quantitative yield. The filtrate was replaced into the reaction flask without isolation of the dichlorophosphatethylmethacrylate intermediate. The reaction flask was then charged with 101 g. (1 mole of dry triethylamine and 73 g. (1 mole) of dry diethylamine. The addition of the two amines was accomplished in the −10° to 10°C. range and afterwards the reaction mixture was stirred at room temperature for 3 days. The solvent and volatile impurities were removed by flash evaporation. The reaction yield or product was 87% of the theoretical. Distillation of the material gave a center cut fraction boiling at 143°–144°C./0.7 mm. pressure. This distiled monomer, Methacryloxyethylorthophosphorotetraethyldiamidate, gave the following analysis: % P calc. 9.70; % P obs. 9.23; % N calc. 8.75, % N obs. 8.20. In three separate runs, different amounts of the monomer (runs A and B with undistilled monomer and run C with distilled monomer) was subjected to graft copolymerizations according to U.S. Pat. No. 3,359,224 onto a rayon knit. The percent conversion of monomer to grafted polymer, and the analysis of the grafted product gave the results reported in Table II appearing at the end of this specification. It was found that distillation aided the grafting efficiency of this monomer. The monomer product is a compound of the general formula in which $R_1$ is $-CH_3$; X and Y = O, $R_2 = -C_2H_4-$ and $R_3$, $R_4$, $R_5$ and $R_6 = CH_3CH_2-$.

EXAMPLE VIII

Example VII involved identical sequence, reaction times, temperature and purification steps to Example VI. The difference between the two procedures involved the use of reactants in a different order of addition. In this Example, the reaction flask was first charged with dry diethyl ether (500 mis.); 76.5 g. (0.5 mole) phosphorus oxychloride; 101 g. (1 mole) dry triethylamine; and 73 g. (1 mole) dry diethylamine. After stirring the reaction mixture at room temperature for 3 days, the triethylamine hydrochloride was filtered off. The filtrate without benefit of purification by distillation was recharged into the reaction flask and reacted in a second step with 68 g. (0.5 mole) hydroxyethylmethacrylate and 50.5 g. (0.5 mole) dry triethylamine. After reacting at room temperature for 72 hours, the product was isolated in 90% yield of the theoretical.

EXAMPLE IX

A 1-liter reaction flask was first charged with dry toluene (500 ml.); 76.5 g. (0.5 mole) phosphorus oxychloride; 101 g. (1 mole) dry triethylamine, and 45 g. (1 mole) dry dimethylamine. After stirring the reaction mixture at room temperature overnight, the triethylamine hydrochloride was filtered off. Vapor phase chromatograph analysis of the filtrate showed the bis (dimethylamido) chlorophosphate to be obtained in 80% yield of the theoretical. A portion of this material free of toluene, 51.3 g. (0.30 mole), was added to a reaction flask containing glycidyl acrylate 32 g. (0.25 mole) in dry acetone at room temperature. The reaction mixture was heated to reflux for 19 hours then cooled to room temperature and the solvent removed via flash evaporation. The residue was then passed through a molecular still using xylene as a solvent to heat the column. The non-volatile fraction was collected in 63.5% yield. This product, which could not be distilled even under reduced pressure without gelation taking place, was found to have an infrared spectrum consistent with its structure. The off-white product was determined to have the following physical properties: $n_D^{20}$ 1.4824; density at 25°C. 1.13; % N calc 9.4%, % N obs. 10.00. The material gave a 30 % conversion of monomer to polymer on carrying out a graft copolymerization according to U.S. Pat. No. 3,359,224 yielding a flame retardant product at 26% polymer add-on as measured by the match test and the Vertical Flame Test (rating of 2, 1¾" char). The product is a compound of the general formula in which $R_1 = N$; X and Y = O; $R_2 = -C_3H_5Cl-$; $R_3, R_4, R_5$ and $R_6 = CH_3-$.

EXAMPLE X

A 1 liter reaction flask was first charged with dry toluene (500 ml.); 76.5 g. (0.5 mole) phosphorus oxychloride; 101 g. (1 mole) dry triethylamine and 45 g. (1 mole) dry dimethylamine. After stirring the reaction mixture at room temperature overnight, the triethylamine hydrochloride was filtered off. Vapor phase chromatographic analyses of the filtrate showed the bis(dimethylamido) chlorophosphate to be obtained in 60% yield of the theoretical. A portion of this material after solvent removal 56.8 g. (0.33 mole) was then reacted in a second step with the hydrochloride of N-(2-aminoethyl) acrylamide 54.8 g. (0.33 mole) in the presence of triethylamine as acid acceptor and benzene as solvent at 70°C. for 6 hours. [The N-(2-aminoethyl) acrylamide hydrochloride was obtained in 84% yield from the reaction of ethylenediamine with methacryloyl chloride at room temperature. Analysis of this hydrochloride intermediate gave % N calc. 17.00, % N obs. 10.01. the infrared spectra was also shown to be consistent with the structure. The melting point was determined to be greater than 270°C.]. After removal of solvent via flash evaporator, the residue was distilled to give a boiling point of 84°–85°C. at 4 mm pressure. The purified material was recovered in 31% yield. An infrared spectrum was shown to be consistent with the structure. The product was determined to have the following physical properties: index of refraction at 20°C 1.4647; density at 25°C. 1.1189, % p calc. 11.6%, % P ohs. 11.7%. The material is a compound of the general formula in which $R_1 = H$; X and $Y = -NH-$; $R_2 = -C_2M_4-$ and $R_3, R_4, R_5$ and $R_6 = -CH_3$.

The material gave a 15% conversion of monomer to polymer on carrying out a graft copolymerization according to U.S. Pat. No. 3,359,224 yielding a flame retardant product at 36% polymer add-on as measured by match test and the Vertical Flame Test (rating of 2, 1½" char).

EXAMPLE XI

A 1 liter reaction flask was first charged with dry toluene (500 ml.); 76.5 q. (0.5 mole) phosphorus oxychloride; 101 g. (1 mole) dry triethylamine, and 45 g. (1 mole) dry dimethylamine. After stirring the reaction mixture at room temperature overnight, the triethylamine hydrochloride was filtered off. Vapor phase chromatographic analysis of the filtrate showed the bis(dimethylamido) chlorophosphate to be obtained in 80% yield of the theoretical. A portion of this material free of toluene, 56.8 g. (0.33 mole) was added to a reaction flask containing anhydrous N-Methylolacrylamide 33.3 g. (0.33 mole), benzene, and triethylamine as acid acceptor. The rection mixture was heated to reflux for 6 hours, cooled to room temperature, and filtered to remove solid amine hydrochloride. Solvent was then removed from the filtrate by flash evaporation and the residue distilled to give a boiling point of 100°–101°C. at 4 mm. pressure. The purified material was recovered in 24% yield. The product is a compound of the general formula in which $R_1 = H$: X $= -NH-$; $Y = O$; $R_2 = -CH_2-$ and $R_3, R_4, R_5$ and $R_6 = -CH_3$. An infrared spectrum was shown to be consistent with the structure. The product was determined to have the following physical properties: index of refraction at 20°C 1.4652; density at 25°C. 1.1300 % N calc 17.9, % N obs. 17.9. The material gave A 20% conversion of monomer to polymer on carrying out a graft copolymerization according to U.S. Pat. No. 3,359,224 yielding a flame retardant product at 35% add-on as measured by match test and the vertical Flame Test (rating of 2, 1¾" char).

EXAMPLE XII

A sample of the monomer prepared in Example IX was graft copolymerized with a cotton knit fabric according to the teachings of U.S. Pat. No. 3,359,224. A grafting efficiency of 38% was achieved giving a flame retardant product (2½" char, rating of 2) at a polymer content of 21.8% based upon the weight of the craft copolymerized product.

EXAMPLE XIII

A sample of the monomer prepared in Example VIII was graft copolymerized with a cotton/polyester blend (65.35) according to the teachings of U.S. Pat. No. 3,359,224. A crafting efficiency of 58% was achieved giving a flame retardplant product (2¾" char, rating of 3) at a polymer content of 25.7% based upon the weight of the graft copolymerized product.

EXAMPLE A

A sample of diethylphosphonomethyl methacrylate monomer was graft copolymerized with a rayon knit fabric according to the teachings of U.S. Pat. No. 3,359,224. A grafting efficiency of 90% was achieved with sufficient monomer to result in 5.92% phosphorus added onto the substrate. A poor rating was achieved on the vertical flame test (5" test (5" tear length, rating of 5).

TABLE 1

| Run | Grafting Efficiency, % | 0 Washes | | 50 Washes | | Vertical Plane | |
|---|---|---|---|---|---|---|---|
| | | % P obs. | % H obs. | % P obs. | % H obs. | Char. | Rating |
| 111A | 56 | 2.00 | 1.32 | (a) | (a) | 1¼" | 2 |
| 111B | 61 | 1.82 | 1.23 | 2.19 | 1.15 | ⅝" | 1 |
| 111C | 59 | 2.09 | 1.43 | 2.42 | 1.44 | ¾" | 1 |
| Ex 4 | 100 | 2.00 | (a) | (a) | (a) | (b) | (b) |

(a) Not tested
(b) Vertical flame not tested, sample self-extinguishing to a flame generated by a lighted match.

TABLE II

| Run | Grafting Efficiency | % P calc. | 0 Washes % P obs. | 50 Washes % P obs. | % H calc. | 0 Washes % N obs. | Vertical Char | Plane Rating |
|---|---|---|---|---|---|---|---|---|
| A | 64 | 2.17 | 2.12 | (a) | 1.96 | 1.27 | 1⅞" | 2 |
| B | 43 | 2.66 | 2.46 | (a) | 2.40 | 1.61 | 1½" | 2 |
| C | 73 | 1.60 | 1.62 | 1.81 | 1.44 | 1.44 | 1⅞" | 2 |

(a) Not tested.

We claim:

1. A compound having the general formula:

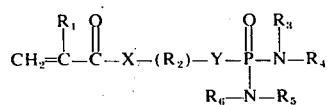

wherein $R_1$ is hydrogen or methyl; $R_2$ is a substituted or unsubstituted lower alkylene group; $R_3$, $R_4$, $R_5$ and $R_6$ are independently selected from either methyl or ethyl; X is oxygen or —NH— and Y is oxygen or —NH—.

2. The compound of claim 1 in which $R_2$ is —$C_2H_4$—; $R_1$, $R_3$, $R_4$, $R_5$ and $R_6$ are all methyl; and X and Y are both oxygen.

3. The compound of claim 1 in which $R_1$ is methyl; X and Y are both oxygen: $R_2$ is —$C_2H_4$—; and $R_3$, $R_4$, $R_5$ and $R_6$ are ethyl.

4. The compound of claim 1 in which $R_1$ is hydrogen; X and Y are both oxygen, $R_2$ is —$C_3H_5Cl$—; $R_2$, $R_3$, $R_4$ and $R_5$ are methyl.

5. The compound of claim 1 in which $R_1$ is hydrogen; X and Y are both —NH—, $R_2$ is —$C_2H_4$—; and $R_3$, $R_4$, $R_5$ and $R_6$ are all methyl.

6. The compound of claim 1 in which $R_1$ is hydrogen; X is —NH—; Y is oxygen; $R_2$ is —$CH_2$—; and $R_3$, $R_4$, $R_5$, and $R_6$ are all methyl.

* * * * *

UNITED STATES PATENT OFFICE
CERTIFICATE OF CORRECTION

Patent No. 3,969,440          Dated July 13, 1976

Inventor(s) N. A. Edelson and R. W. Faessinger

It is certified that error appears in the above-identified patent and that said Letters Patent are hereby corrected as shown below:

Column 2, line 51, change "M." to --N.--;
         line 53, change "Paessinger" to --Faessinger--.
Column 3, line 4, change "substrates" to --substrate--;
         line 7, change "1.5" to --1.5%--;
         line 9, change "3.5" to --3.5%-- and change "5.6%" to --5.0%--;
         line 27, change "less" to --loss--.
Column 4, line 7, change "23°" to --93°--;
         line 37, change "Knit" to --knit--.
Column 5, line 1, change "59" to --50--;
         line 16, change "50%" to --59%--;
         line 25, change "$Ca(NH_4)_2$" to --$Ce(NH_4)_2$--;
         line 34, change "3" to --2--;
         line 58, change "62" to --68--.
Column 6, line 4, change "or" to --of--;
         line 7, change "distiled" to --distilled--;
         line 24, change "sequence" to -reagents--;
         line 64, change "1.13" to --1.18--.
Column 7, line 15, change "60%" to --80%--;
         line 25, change "10.01" to --16.61-- and change "the" to --The--.
         line 34, change "p" to --P-- and change "11.6%" to --11.8%--;
         line 35, change "ohs." to --obs.--;
         line 37, change "$-C_2M_4-$" to -- $-C_2H_4-$ --;
         line 47, change "q." to --g.--
         line 52, change "analysis" to --analyses--.
Column 8, line 6, change "rection" to --reaction--;
         line 19, change "A" to --a--;
         line 23, change "vertical" to --Vertical--;
         line 32, change "craft" to --graft--;
         line 39, change "crafting" to --grafting--;
         line 51, delete "(5" test".

UNITED STATES PATENT OFFICE
CERTIFICATE OF CORRECTION

Patent No. 3,969,440     Dated July 13, 1976

Inventor(s) N. A. Edelson and R. W. Faessinger

It is certified that error appears in the above-identified patent and that said Letters Patent are hereby corrected as shown below:

Table I, in the headings, change "%H obs." to --%N obs.--, both occurrences;
    in the line beginning 111A change "2.00" to --2.08-- and also change "1.32" to --1.82--;
    in the line beginning 111B change "2.19" to --2.18--;
    in the line beginning Ex 4 change "2.00" to --2.99--.

Table 2, in the heading, change "%H calc." to --%N calc.-- and change "Vertical Plane" to --Vertical Flame--.

Column 9, line 25, after "-NH-" add a semicolon(;) and change the comma "," to a period(.).

Column 10, line 14, change ":" to a semicolon(;);
    line 17, change "," to a semicolon(;).

Signed and Sealed this

Thirty-first Day of October 1978

[SEAL]

Attest:

RUTH C. MASON
Attesting Officer

DONALD W. BANNER
Commissioner of Patents and Trademarks